United States Patent
Senetar et al.

(10) Patent No.: US 6,444,869 B2
(45) Date of Patent: *Sep. 3, 2002

(54) PROCESS FOR PRODUCING ETHYLENE

(75) Inventors: John J. Senetar, Naperville; Lawrence W. Miller, Palatine; Linda Shi Cheng; Mark M. Davis, both of Chicago, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/909,249

(22) Filed: Jul. 19, 2001

Related U.S. Application Data

(62) Division of application No. 09/411,123, filed on Oct. 4, 1999, now Pat. No. 6,303,841.

(51) Int. Cl.$^7$ .............................. C07C 7/00; C07C 1/20
(52) U.S. Cl. ...................... 585/809; 585/802; 585/638; 585/639; 585/640; 585/820; 585/822
(58) Field of Search .............................. 585/809, 802, 585/638, 639, 640, 820, 822, 833

(56) References Cited

U.S. PATENT DOCUMENTS

| | | | |
|---|---|---|---|
| 3,055,183 A | 9/1962 | Kniel .............................. 62/17 |
| 3,176,444 A | 4/1965 | Kiyonaga ........................ 55/26 |
| 3,430,418 A | 3/1969 | Wagner ........................... 55/25 |
| 3,703,068 A | 11/1972 | Wagner ........................... 55/21 |
| 3,928,483 A | 12/1975 | Chang et al. ............. 260/668 R |
| 3,986,849 A | 10/1976 | Fuderer et al. .................. 55/25 |
| 4,025,575 A | 5/1977 | Chang et al. ................ 260/682 |
| 4,052,479 A | 10/1977 | Chang et al. ................ 260/682 |
| 4,310,440 A | 1/1982 | Wilson et al. ............... 252/435 |
| 4,368,061 A * | 1/1983 | Mestrallet et al. ............. 62/630 |
| 4,440,871 A | 4/1984 | Lok et al. .................... 502/214 |
| 4,447,669 A | 5/1984 | Hamon et al. ................ 585/640 |
| 4,464,189 A * | 8/1984 | Teddar ......................... 62/628 |
| 4,496,786 A | 1/1985 | Santilli et al. ............... 585/640 |
| 4,499,314 A | 2/1985 | Seddon et al. ............... 585/408 |
| 4,499,327 A | 2/1985 | Kaiser ......................... 585/640 |
| 4,547,616 A | 10/1985 | Avidan et al. ............... 585/640 |
| 4,554,143 A | 11/1985 | Messina et al. .............. 423/306 |
| 4,677,242 A | 6/1987 | Kaiser ......................... 585/638 |
| 4,677,243 A | 6/1987 | Kaiser ......................... 585/638 |
| 4,752,651 A | 6/1988 | Kaiser ......................... 585/640 |
| 4,793,984 A | 12/1988 | Lok et al. .................... 423/306 |
| 4,843,183 A | 6/1989 | Inui ............................. 585/640 |
| 4,853,197 A | 8/1989 | Wilson et al. ............... 423/306 |
| 4,861,938 A | 8/1989 | Lewis et al. ................. 585/640 |
| 4,873,390 A | 10/1989 | Lewis et al. ................. 585/638 |
| 4,895,584 A | 1/1990 | Buck et al. ..................... 62/29 |
| 4,973,792 A | 11/1990 | Lewis et al. ................. 585/638 |
| 5,095,163 A | 3/1992 | Barger ......................... 585/640 |
| 5,126,308 A | 6/1992 | Barger et al. ................ 502/214 |
| 5,191,141 A | 3/1993 | Barger et al. ................ 585/640 |
| 5,245,099 A | 9/1993 | Mitariten .................... 585/650 |
| 5,332,492 A | 7/1994 | Maurer et al. ............... 208/340 |
| 5,365,011 A | 11/1994 | Ramachandran et al. ... 585/829 |
| 5,470,925 A | 11/1995 | Ramachandran et al. ..... 526/68 |
| 5,744,687 A | 4/1998 | Ramachandran et al. ... 585/829 |
| 5,811,621 A | 9/1998 | van Dijk ..................... 585/639 |
| 5,879,431 A | 3/1999 | Baker et al. .................... 95/50 |
| 5,914,433 A | 6/1999 | Marker ........................ 585/313 |
| 5,960,643 A | 10/1999 | Kuechler et al. .............. 62/620 |
| 5,990,369 A | 11/1999 | Barger et al. ................ 585/640 |
| 6,212,905 B1 | 4/2001 | Kuechler et al. .............. 62/630 |
| 6,303,841 B1 * | 10/2001 | Senetar et al. ............... 585/638 |

OTHER PUBLICATIONS

Article "Better Ethylene Separation Unit" by V. Kaiser et al., *Hydrocarbon Processing*, Nov. '88, pp. 57–61.
Donald W. Breck, *Zeolite Molecular Sieves*, published by Robert E. Krieger Publishing Company, Malabar, Florida.

* cited by examiner

*Primary Examiner*—Walter D. Griffin
(74) *Attorney, Agent, or Firm*—John G. Tolomei; Frank S. Molinaro; Mark Goldberg

(57) ABSTRACT

A process is provided for the concentration and recovery of ethylene and heavier components from an oxygenate conversion process. A separation process such as a pressure swing adsorption (PSA) process is used to remove hydrogen and methane from a demethanizer overhead stream comprising hydrogen, methane and C$_2$ hydrocarbons and subsequently return the recovered C$_2$ hydrocarbons to be admixed with the effluent from the oxygenate conversion process. This integration of a separation zone with a fractionation scheme in an ethylene recovery scheme using an initial demethanizer zone resulted in significant capital and operating cost savings by the elimination of cryogenic ethylene-based refrigeration from the overall recovery scheme.

17 Claims, 6 Drawing Sheets

PROCESS FOR PRODUCING ETHYLENE

CROSS-REFERENCE TO RELATED APPLICATION

This application is a Division of application Ser. No. 09/411,123 filed Oct. 4, 1999, now U.S. Pat. No. 6,303,841, the contents of which are hereby incorporated by reference.

FIELD OF THE INVENTION

The present invention relates to a process for the production of light olefins from the effluent of an oxygen conversion process. More particularly, the present invention relates to a process for the recovery of high purity ethylene from the reactor effluent of an oxygenate conversion process.

BACKGROUND OF THE INVENTION

Light olefins serve as the building blocks for the production of numerous chemicals. Light olefins have traditionally been produced through the process of steam or catalytic cracking. The search for alternative materials for light olefin production has led to the use of oxygenates such as alcohols, and more particularly to the use of methanol, ethanol and higher alcohols or their derivatives wherein these compounds are converted to light olefins. The alcohols may be produced by fermentation or from synthesis gas. Synthesis gas can be produced from natural gas, petroleum liquids and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. No. 3,928,483 B1, U.S. Pat. No. 4,025,575 B1, U.S. Pat. No. 4,052,479 B1 (Chang et al.); U.S. Pat. No. 4,496,786 B1 (Santilli et al.); U.S. Pat. No. 4,547,616 B1 (Avidan et al.); U.S. Pat. No. 4,677,243 B1 (Kaiser); U.S. Pat. No. 4,843,183 B1 (Inui); U.S. Pat. No. 4,499,314 B1 (Seddon et al.); U.S. Pat. No. 4,447,669 B1 (Hamon et al.); U.S. Pat. No. 5,095,163 B1 (Barger); U.S. Pat. No. 5,191,141 B1 (Barger et al.); U.S. Pat. No. 5,126,308 B1 (Barger et al.); U.S. Pat. No. 4,973,792 B1 (Lewis et al.); and U.S. Pat. No. 4,861,938 B1 (Lewis et al.). U.S. Pat. No. 4,861,938 B1 and U.S. Pat. No. 4,677,242 B1 particularly emphasize the use of a diluent combined with the feed to the reaction zone to maintain sufficient catalyst selectivity toward the production of light olefin products, particularly ethylene. The above U.S. patents are hereby incorporated by reference.

The product produced by the oxygenate conversion process is a light gas stream containing lighter components (e.g. hydrogen, nitrogen, etc.) methane, ethane and a substantial quantity of hydrocarbons of higher molecular weight, for example, propane, butane, pentane and often their unsaturated analogs. Separation of these components to recover ethylene requires a complex energy intensive scheme, thus creating a need for more efficient separation processes which yields higher recovery levels of ethylene. In typical ethylene plant recovery sections, where the ethylene production is based on the pyrolysis of naphtha or gas oil, the use of cryogenic processes utilizing the principle of gas expansion through a mechanical device to produce power while simultaneously extracting heat from the system have been employed. The use of such equipment varies depending upon the pressure of the product gas stream, the composition of the gas and the desired end results. In the typical cryogenic expansion-type recovery processes used in the prior art, a gas stream is withdrawn from the pyrolysis furnace, compressed and cooled. The cooling is accomplished by heat exchange with other streams of the process and/or external sources of cooling are employed such as refrigeration systems. As the product gas is cooled, liquids are condensed, collected and separated so as to thereby obtain desired hydrocarbons. The high-pressure liquid stream so recovered is typically transferred to a demethanizer column after the pressure is adjusted to the operating pressure of the demethanizer. In such a fractionating column, the high-pressure liquid stream is fractionated to separate the residual methane and lighter components from the desired products of ethylene and heavier hydrocarbon components. In the ideal operation of such separation processes, the vapors, or light cut, leaving the process contain substantially all of the methane and lighter components found in the feed gas and substantially no ethylene and heavier hydrocarbon components remain. The bottom fraction, or heavy cut, leaving the demethanizer typically contains substantially all of the ethylene and heavier hydrocarbon components with very little methane or lighter components which are discharged in the fluid gas outlet from the demethanizer. A typical combined gas expansion and fractionation process for the separation of hydrocarbon gas stream comprising components ranging from nitrogen through $C_3$-plus hydrocarbons into a methane and lighter stream and an ethylene and heavier stream is exemplified by U.S. Pat. No. 4,895,584 B1. A typical ethylene separation section of an ethylene plant containing both cryogenic and fractionation steps to recover an ethylene product with a purity exceeding 99.5% ethylene is described in an article by V. Kaiser and M. Picciotti entitled, "Better Ethylene Separation Unit," appeared in Hydrocarbon Processing, November 1988, pages 57–61 and is herein incorporated by reference.

Pressure swing adsorption (PSA) provides an efficient and economical means for separating a multi-component gas stream containing at least two gases having different adsorption characteristics. The more strongly adsorbable gas can be an impurity which is removed from the less strongly adsorbable gas which is taken off as product; or, the more strongly adsorbable gas can be the desired product, which is separated from the less strongly adsorbable gas. For example, it may be desired to remove carbon monoxide and light hydrocarbons from a hydrogen-containing feed stream to produce a purified (99+%) hydrogen stream for a hydrocracking or other atalytic process where these impurities could adversely affect the catalyst or the reaction. On the other hand, it may be desired to recover more strongly adsorbable gases, such as ethylene from a feed stream to produce an ethylene-rich product.

In PSA, a multi-component gas is typically fed to at least one of a plurality of adsorption zones at an elevated pressure effective to adsorb at least one component, while at least one other component passes through. At a defined time, the feed stream to the adsorber is terminated and the adsorption zone is depressurized by one or more co-current depressurization steps wherein pressure is reduced to a defined level which permits the separated, less strongly adsorbed component or components remaining in the adsorption zone to be drawn off without significant concentration of the more strongly adsorbed components. Then, the adsorption zone is depressurized by a counter-current depressurization step wherein the pressure on the adsorption zone is further reduced by withdrawing desorbed gas counter-currently to the direction of the feed stream. Finally, the adsorption zone is purged and repressurized. The combined gas stream produced during the counter-current depressurization step and the purge step is typically referred to as the tail gas stream. The final stage of repressurization is typically performed by introducing a slipstream of product gas comprising the lightest gas component produced during the adsorption step. This final stage of repressurization is often referred to as product repressurization. In multi-zone systems, there are typically additional steps, and those noted above may be done in stages. U.S. Pat. No. 3,176,444 B1 issued to Kiyonaga, U.S. Pat. No. 3,986,849 B1 issued to Fuderer et al., and U.S. Pat. No. 3,430,418 B1 and U.S. Pat. No. 3,703,068 B1 both issued to Wagner, among others, describe multi-zone, adiabatic PSA systems employing both co-current and counter-current depressurization, and the disclosures of these patents are incorporated by reference in their entireties.

Various classes of adsorbents are known to be suitable for use in PSA systems, the selection of which is dependent upon the feed stream components and other factors generally known to those skilled in the art. In general, suitable adsorbents include molecular sieves, silica gel, activated carbon and activated alumina. When PSA processes are used to purify hydrogen-containing streams, the hydrogen is essentially not adsorbed on the adsorbent. However, when purifying methane-containing streams, methane is often adsorbed on the adsorbent along with the impurity.

Numerous patents disclose the use of PSA in combination with fractionation to separate hydrogen and methane from heavier hydrocarbons. U.S. Pat. No. 5,245,099 B1, which is hereby incorporated by reference, discloses a process for the concentration and recovery of ethylene and heavier components from a hydrocarbon feed stream. A PSA process is used to remove from hydrocarbon feed stream light cut comprising hydrogen, carbon monoxide and methane and subsequently concentrate a heavy cut comprising the ethylene and heavy components in the PSA tail gas. In one aspect of the invention, an FCC off gas is separated into a light cut and a heavy cut and the heavy cut is routed to an ethylene plant.

U.S. Pat. No. 5,332,492 B1 discloses a process for recovering hydrogen-rich gases and increasing the recovery of liquid hydrocarbon products from a hydrocarbon conversion zone effluent by the particular arrangement of refrigeration and PSA steps and two vapor-liquid, or flash, separation zones.

U.S. Pat. No. 5,365,011 B1, U.S. Pat. No. 5,470,925 B1 and U.S. Pat. No. 5,744,687 B1 disclose a process for the integration of a PSA zone containing an adsorbent selective for the adsorption of ethylene and propylene from a catalytic cracking process at an adsorption temperature above 50° C. to about 250° C. The adsorbent is selected from the group consisting of zeolite 4A, zeolite 5A, zeolite 13X and mixtures thereof.

The existing cryogenic and fractionation system in a typical ethylene recovery scheme can be employed in an oxygenate conversion process to recover ethylene, but the penalties of this operation are significant. The low level of light components such as hydrogen and methane relative to ethylene plant product compositions still are high enough to significantly raise the compression and refrigeration requirements in the recovery section of the oxygenate conversion plant for the incremental amount of ethylene recovered. Thus, recovering ethylene from oxygenate conversion effluent is an expensive and complex process involving extensive compression and fractionation to separate the light gases such as hydrogen and methane from the ethylene. Processes are sought which enable the concentration and recovery of the ethylene and heavier components from oxygenate conversion effluent without expensive compression and cryogenic separation steps to remove the lighter components.

SUMMARY OF THE INVENTION

The use of conventional methods developed for ethylene separation when applied to separate ethylene produced from an oxygenate conversion process effluent stream will result in a separation zone of higher capital cost and higher operating cost than required. It was discovered that the unique character of the oxygenate conversion process effluent stream allowed the use of a separation process to further concentrate and recover ethylene. For example, when a separation zone which employed a deethanization zone as an initial separation followed by a demethanization zone to recover a $C_2$ hydrocarbon stream was combined with a separation process to further process the demethanizer overhead stream, significant savings in the demethanizing step could be obtained by a warmer demethanizer operation, and the desorbed ethylene was returned to be combined with the oxygenate conversion effluent stream. In the conventional ethylene separation train, the demethanizer is required to operate at demethanizing conditions, including a demethanizer temperature which is sufficiently cold enough to provide a reasonable split between methane and ethylene. Typically, a demethanizer temperature less than about −95° C. (−140° F.) is required to recover ethylene in the presence of a large amount of methane and hydrogen. Applicant discovered that by employing an initial demethanizer separation in the ethylene recovery zone with a separation process such as a PSA zone wherein the PSA zone contained an adsorbent which was selective for the adsorption of ethylene relative to methane and hydrogen, and the desorbed stream was recombined with the oxygenate conversion process effluent stream, the demethanizer temperature could be increased to about −40° C. with significant overall process benefits. This savings appears to be greatest in the separation of components such as ethylene from oxygenate conversion process effluent streams wherein the critical molar ratio of materials more volatile than ethylene, such as hydrogen and methane, to the total moles of ethylene and ethane is less than about 0.5.

In one embodiment, the present invention is a process for the production of ethylene from an oxygenate conversion effluent stream. The oxygenate conversion effluent stream comprises hydrogen, methane, ethylene, ethane, propylene, propane and $C_4$-plus olefins. The process of the present invention comprises a number of processing steps. The oxygenate conversion effluent stream is passed to a demethanizer zone to provide a light hydrocarbon feed stream comprising hydrogen, methane, ethylene and ethane, and a deethanized stream comprising propylene, propane and $C_4$-plus olefins. The light hydrocarbon stream is passed to a demethanizer zone operating at a demethanizing temperature greater than about −45° C. to provide a bottom stream comprising ethylene and ethane and an overhead stream comprising hydrogen, methane and ethylene. The overhead stream at effective adsorption conditions is passed to an adsorption zone containing at least two adsorption beds. Each of the adsorption beds contains a selective adsorbent to adsorb the ethylene. On adsorption, the adsorption beds produce an adsorber effluent stream comprising hydrogen and methane. On desorption, the adsorption beds produce a desorbed stream comprising ethylene. The bottom stream is passed to a $C_2$ splitter zone to produce an ethylene product stream and an ethane stream. At least a portion of the desorption stream is combined with the oxygenate conversion effluent stream prior to passing the oxygenate conversion effluent stream to the demethanizer zone

DETAILED DESCRIPTION OF THE INVENTION

Figure 1:
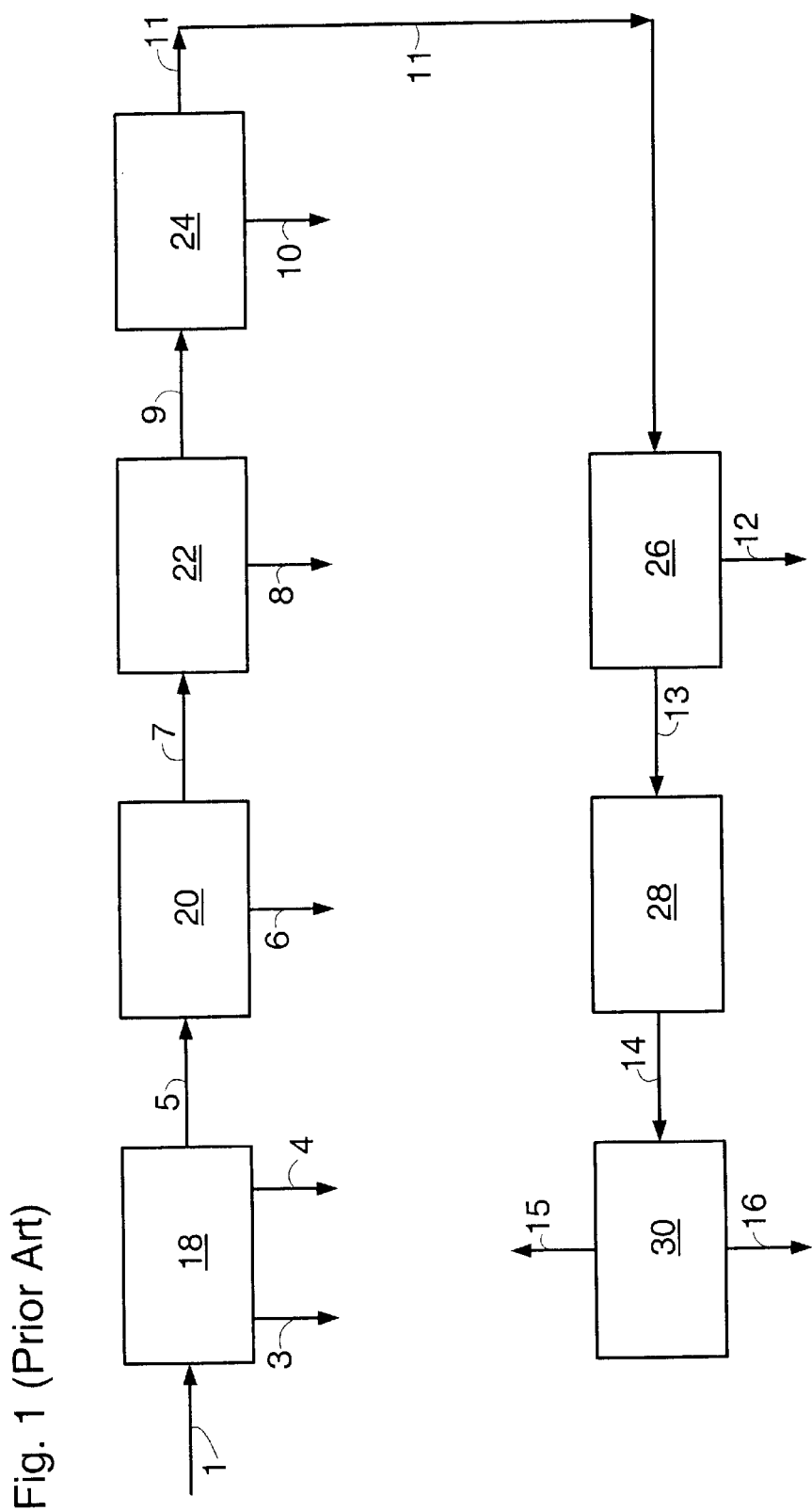
FIG. 1 is a schematic process flow diagram illustrating the process of the prior art for recovering light olefins from an oxygenate conversion process.

This invention relates to recovery schemes used in conjunction with a process for the catalytic conversion of a feedstock comprising one or more aliphatic hetero compounds comprising alcohols, halides, mercaptans, sulfides, amines, ethers and carbonyl compounds or mixtures thereof to a hydrocarbon product containing light olefinic products, i.e., $C_2$, $C_3$ and/or $C_4$ olefins. The feedstock is contacted with a silicoaluminophosphate molecular sieve at effective process conditions to produce light olefins. Silicoaluminophosphate (SAPO) molecular sieves which produce light olefins are generally employable in the instant process. The preferred silicoaluminophosphates are those described in U.S. Pat. No. 4,440,871 B1. Silicoaluminophosphate molecular sieves employable in the instant process are more fully described hereinafter.

The oxygenate conversion step of the present invention is preferably conducted in the vapor phase such that the oxygenate feedstock is contacted in a vapor phase in a reaction zone with a molecular sieve catalyst at effective process conditions to produce hydrocarbons, i.e., an effective temperature, pressure, weight hourly space velocity (WHSV) and, optionally, an effective amount of diluent, correlated to produce hydrocarbons. The process is affected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. Reaction conditions for the conversion of aliphatic hetero compounds can be determined by those skilled in the art and preferably, in accordance with the present invention, comprise a temperature of from about 200° to 600° C., more preferably from about 300° to 500° C., and a pressure of from about 7 kPa to about 1.4 Mpa (1 to 200 psia), more preferably from about 140 kPa to about 700 kPa (20 to 100 psia). Typical processes for producing light olefins are described U.S. Pat. No. 4,499,327 B1 and U.S. Pat. No. 4,873,390 B1 cited above and hereby incorporated by reference.

The selection of a particular catalyst for use in the oxygenate conversion step depends upon the particular oxygenate conversion desired but in a preferred aspect of the present invention where the oxygenate feedstock is converted into light olefins, it is preferred that the catalysts have relatively small pores. Certain of the catalysts useful in the present invention have pores with an average effective diameter of less than 5 Å. The average effective diameter of the pores of preferred catalysts is determined by measurements described in D. W. Breck, ZEOLITE MOLECULAR SIEVES by John Wiley & Sons, New York (1974), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves and non-zeolitic molecular sieves.

Zeolitic molecular sieves in the calcined form may be represented by the general formula:

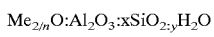

$$Me_{2/n}O:Al_2O_3:xSiO_2:yH_2O$$

where Me is a cation, x has a value from about 2 to infinity, n is the cation valence and y has a value of from about 2 to 10. Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11 and MCM-22. Other zeolites include those having a high silica content, i.e., those having silica-to-alumina ratios greater than and typically greater than 100 can also be used. Detailed descriptions of some of the above-identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of elements, x represents the total amount of the metal mixture present. Preferred elements (EL) are silicon, magnesium and cobalt with silicon being especially preferred. The preparation of various ELAPOs is well-known in the art and may be found in U.S. Pat. No. 5,191,141 B1 (ELAPO); U.S. Pat. No. 4,554,143 B1 (FeAPO); U.S. Pat. No. 4,440,871 B1 (SAPO); U.S. Pat. No. 4,853,197 B1 (MAPO, MnAPO, ZnAPO, COAPO); U.S. Pat. No. 4,793,984 B1 (CAPO), U.S. Pat. No. 4,752,651 B1 and U.S. Pat. No. 4,310,440 B1, all of which are incorporated by reference. A preferred embodiment of the invention is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. No. 4,440,871 B1; U.S. Pat. No. 5,126,308 B1 and U.S. Pat. No. 5,191,141 B1. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane and water but does not adsorb isobutane, indicating that it has a pore opening of greater than about 4.3 Å and less than about 5.0 Å.

The molecular sieve catalyst for the oxygenate conversion zone preferably is incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials and mixtures thereof to provide a desired property or properties, e.g., desired catalyst dilution, mechanical strength and the like to the solid particles. Such matrix materials are often, to some extent, porous in nature and may or may not be effective to promote the desired hydrocarbon conversion. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like. The preparation of solid particles comprising catalyst and matrix materials is conventional and well known in the art and, therefore, need not be discussed in detail herein.

The oxygenate conversion reaction is preferably carried out in a bubbling bed or a fluidized bed reaction zone wherein feed and catalyst are contacted at effective oxygenate conversion conditions. During the oxygenate conversion reaction, a carbonaceous material—i.e., coke—is deposited on the catalyst. The carbonaceous deposit material has the effect of reducing the number of active sites on the catalyst which thereby affects the extent of the conversion. During the conversion process, a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 wt-%, or only partially regenerate the catalyst, e.g., to from about 2 to 30 wt-% carbon. Preferably, the regenerated catalyst will contain about 0 to 20 wt-% and more preferably from about 0 to 10 wt-% carbon. Additionally, during regeneration, there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration.

The oxygenate conversion effluent which comprises products obtained from the conversion process will, of course, depend, for example, on the feed stream, catalyst and conditions employed. Preferably, the desired product is organic. The organic product or products are preferably hydrocarbons in the $C_2$ to $C_6$ carbon range. In one aspect, the desired product preferably contains light olefins having from about 2 to 6, more preferably from about 2 to 4 carbon atoms per molecule. The desired product or products preferably have kinetic diameters which allow such product or products to be removed from or escape from the pores of the catalyst. Generally, the oxygenate conversion effluent comprises hydrogen, methane, carbon monoxide, carbon dioxide, ethylene, ethane, propylene, propane and $C_4$-plus hydrocarbons such as butenes and butane. Preferably, the molar ratio of hydrogen and methane to the moles of ethylene and ethane in the oxygenate conversion effluent is less than about 0.5. More preferably, the molar ratio of hydrogen and methane to the moles of ethylene and ethane in the oxygenate conversion effluent is between about 0.01 to about 0.5. It is believed that this particular range of the ratio of moles of hydrogen and methane to the moles of ethylene and ethane in the oxygenate conversion effluent stream combined with the relatively high ratio of ethylene to ethane in the $C_2$ hydrocarbons permits the ncorporation of a separation zone for the separation of the ethylene from a emethanizer overhead stream in a scheme for the production of a high purity ethylene roduct by the recovery of ethylene from the demethanizer bottoms in a $C_2$ splitter zone. The separation zone can comprise a temperature swing adsorption zone, a pressure swing adsorption zone, a membrane separation zone, a vacuum swing adsorption zone, a liquid absorption system and combinations thereof.

In the present invention, the oxygenate conversion effluent stream comprising hydrogen, carbon dioxide, water, $C_2$ to $C_4$ hydrocarbons and oxygenates such as dimethyl ether (DME), is withdrawn from the oxygenate conversion reactor and passed to a multi-stage effluent compressor to raise the pressure of the oxygenate conversion effluent stream to provide a compressed effluent stream. The compressed effluent stream is passed to an oxygenate removal zone for the recovery of any DME and unreacted oxygenate to provide an oxygenate depleted effluent stream. Generally, the oxygenate removal zone comprises the use of conventional water washing and methanol washing steps well known to those skilled in the art. The oxygenate depleted effluent stream is passed to a carbon dioxide removal zone comprising a caustic wash or amine/caustic wash zone for the removal of carbon dioxide. The carbon dioxide depleted stream resulting therefrom is passed to a dryer zone to reduce the water content of the resulting dry effluent stream to less than about 5 ppm-wt water. More preferably, the water content of the resulting dry effluent stream is less than about 1 ppm-wt water. The dry effluent stream is passed to a series of fractionation zones to separate the individual olefins into high purity products. The initial fractionation zone comprises a demethanizer which separates the oxygenate conversion effluent into an overhead stream comprising hydrogen, carbon monoxide, methane, acetylene, ethylene, and ethane, and a demethanizer bottoms stream comprising propylene, propane and heavier hydrocarbons. The demethanizer overhead stream is passed to a compression and selective hydrogenation zone to compress and selectively hydrogenate or saturate the acetylene in the presence of hydrogen and produce a treated demethanizer overhead stream which is essentially free of acetylene. Acetylene is removed to minimize the possibility of an explosion hazard by the buildup of acetylenes in the ethylene column and to produce an ethylene product that is essentially free of acetylene. By the term "essentially free of acetylene", it is meant having an acetylene concentration of less than about 1 ppm-wt acetylene. The treated demethanizer overhead stream, now depleted in acetylene relative to the oxygenate conversion effluent stream, is passed to a demethanizer zone. The demethanizer zone operates at effective demethanizing conditions to provide a demethanizer bottoms stream comprising ethylene having at least a 50:1 ratio of ethylene to ethane. Preferably, the demethanizer zone comprises a primary ethylene recovery of greater than about 85 mol-% ethylene per mole of ethylene in the light hydrocarbon stream, or the feed to the demethanizer zone. The overhead stream from the demethanizer zone is passed to a separation zone. The overhead stream of the present invention preferably comprises a non-adsorbable molar ratio of hydrogen and methane to $C_2$ hydrocarbons less than about 0.2. More preferably, the non-adsorbable molar ratio of hydrogen and methane to $C_2$ hydrocarbons ranges between about 0.07 and about 0.17 which correspond to ethylene recycle ratios of between about 0.1 and 0.2 of the total ethylene produced. According to the present invention, it was unexpectedly discovered that for an overhead stream having a non-adsorbable molar ratio within the above range, the demethanizer can be operated at a demethanizing temperature of greater than about −40° C., rather than the traditional cryogenic demethanizer temperature of about −95° C. (−140° F.). Thus, the overall ethylene separation objectives can be met without using an ethylene refrigerant, without a significant loss of ethylene product, without significant increases in ethylene recycle, and without considerable increases in operating cost and capital cost. Beyond the above non-adsorbable molar ratio range of about 0.5, the recovery requirements of the PSA zone or other type of separation zone increases to about 99.9+ percent, and the amount of ethylene returned to the reactor effluent compressor, or recycled within the entire ethylene recovery zone increases significantly. This is in contrast to a typical naphtha cracking stream wherein the non-adsorbable molar ratio of hydrogen and methane to $C_2$ hydrocarbons ranges between about 1.2 to 1.4 and which would require an overall increase in ethylene recycle ratio to about 1.5 to about 1.7 (150–170 percent of the total ethylene recycle), which would significantly increase the capital and equipment requirements over a scheme according to the present invention. These overall benefits permit the demethanizer zone to be cooled with a propylene refrigerant (<−49° C.) rather than an ethylene refrigerant-based cooling system (<−140° C.) for recovering ethylene from the effluent from an oxygenate conversion zone.

The separation zone which can comprise a solvent absorption zone, a temperature swing adsorption zone, a pressure swing adsorption zone, a vacuum swing adsorption zone, or a membrane separation zone and combinations thereof which selectively separates ethylene and heavier components from a separation zone effluent stream comprising hydrogen, methane and carbon monoxide which is withdrawn as a first fuel gas stream. The ethylene-rich stream is recycled to the product compressor to be combined with the oxygenate conversion effluent stream. When the separation zone comprises a PSA zone, the adsorbent comprises a selective adsorbent such as silica gel, activated carbon, alumina, zeolite and mixtures thereof for the adsorption of ethylene and ethane. Such zeolites may include zeolite type X and zeolite type Y, ion exchanged forms thereof and mixtures thereof. The zinc exchanged form of zeolite of zeolite X and the calcium exchanged form of zeolite Y may be included in the selective adsorbent. It is particularly preferred that the selective adsorbent for the PSA process comprise silica gel and that the adsorption temperature ranges between about −18° C. and about 100° C. More preferably, the adsorption temperature ranges between about −18° C. and about 50° C. And most preferably, the adsorption temperature comprises less than about 49° C. It is believed that at adsorption temperatures above about 100° C., and especially at adsorption temperatures above about 50° C., silica gel becomes less selective for the adsorption of hydrogen and methane relative to $C_2$ hydrocarbons. This adsorption of ethylene over silica gel, surprisingly, behaves in a manner which is opposite to the observed adsorption characteristics of ethylene over a zeolite adsorbent such as zeolite 4A. A comparison of the "delta loading" of ethylene on the adsorbent between the conditions of adsorption and desorption in a PSA cycle illustrated the different behavior of the adsorbents. As used herein, the term "delta loading" is the difference between the amount of adsorbed material on the adsorbent between the adsorption and desorption conditions, as measured in moles per unit weight of adsorbent. Generally, the delta loading is expressed in pound moles per 100 pounds of adsorbent, or gram moles per 100 grams of adsorbent. Silica gel was found to display an increasing delta loading as the adsorption temperature is reduced below about 100° C. On desorption, a desorbed stream comprising ethane and ethylene is withdrawn from the PSA zone. Preferably, the adsorption zone provides an adsorptive recovery of ethylene greater than about 95 mol-% ethylene.

The PSA process is an essentially adiabatic process for separating a multi-component fluid containing at least one selectively adsorbable component. The PSA process of the invention relates to conventional PSA processing in which each bed of an adsorption zone undergoes, on a cyclic basis, high-pressure adsorption, optional co-current depressurization to intermediate pressure level(s) with release of void space gas from the product end of the bed, counter-current depressurization to lower desorption pressure with the release of desorbed gas from the feed end of the bed, with or without purge of the bed, and repressurization to higher adsorption pressure. The process of the present invention adds to this basic cycle sequence the use of a co-current depressurization, or vent step, in the adsorption zone in which the less readily adsorbable component is further and preferably essentially completely removed therefrom. The adsorption zone is then counter-currently depressurized to a desorption pressure that is at or above atmospheric pressure with the more adsorbable component(s) being discharged from the feed end thereof as a product of desired purity. Those skilled in the art will appreciate that the high-pressure adsorption step of the PSA process comprises introducing the PSA feed stream, or the demethanizer overhead stream, to the feed end of the adsorbent bed at a high adsorption pressure. The less readily adsorbable components (hydrogen and methane) pass through the bed and are discharged from the product end thereof. An adsorption front or fronts are established in the bed with said fronts likewise moving through the bed from the feed end toward the product end thereof. When the feed stream contains a less readily adsorbable component and a more readily adsorbable component, a leading adsorption front of the more readily adsorbable component will be established and move through the bed in the direction of the product or discharge end thereof.

The PSA feed stream or demethanizer overhead stream of this invention comprises from about 10 to about 60 mol-% hydrogen, from about 5 to 50 mol-% methane and from about 10 to 60 mol-% ethylene and heavier components. In the adsorption zone, the more readily adsorbable components are adsorbed at an adsorption pressure and adsorption temperature and the less readily adsorbable components are passed through the adsorption zone. The adsorption zone pressure ranges from about 350 kPa to about 3.5 MPa (about 50 to about 500 psia). The adsorption zone temperature is any temperature effective to adsorb the more readily adsorbable components in the feed stream, and preferably from about −18° C. to less than about 50° C. (about 0° to about 120° F.). It is to be understood that the adsorption zones of the present invention contain adsorber beds containing adsorbent suitable for adsorbing the particular components to be adsorbed therein. As the capacity of the adsorber bed for the more readily adsorbable component is reached, that is, preferably before a substantial portion of the leading adsorption front has passed through the first adsorber bed, the PSA feed stream is directed to another bed in the adsorption zone. It is to be also understood that the term "countercurrent" denotes that the direction of gam flow through the adsorption zone, i.e., adsorber bed, is counter-current with respect to the direction of PSA feed stream flow. Similarly, the term "co-current" denotes flow iIL the same direction as the PSA feed stream flow. The purge gas is at least partially comprised of an effluent stream, e.g., the adsorption effluent stream or the co-current displacement effluent stream, from the adsorption zone, as hereinafter described, which comprises the less readily adsorbable component. When hydrogen is the less readily adsorbable component, the purge gas is preferably rich in hydrogen at a higher concentration than available in the PSA feed stream. The term "enriched" is intended to be with reference to the PSA feed stream composition unless otherwise noted. Following the adsorption step, the bed undergoes a vent step wherein the bed is allowed to depressurize co-currently to a vent pressure in a direction co-current to the feeding step. By the use of this co-current depressurization step, or vent step, the effluent gas stream is substantially reduced and preferably essentially free of the less readily adsorbable component, thus having a molar concentration of more readily adsorbable components. The less readily adsorbable component that remains in the void spaces of the adsorbent bed ahead of the leading adsorption front can be essentially completely displaced from the bed and can enrich the more readily adsorbed component behind the adsorption front. This enables the more readily adsorbable component to be thereafter discharged from the feed end of the bed as a product of desired purity by counter-currently depressurizing the bed. The co-current depressurization step can be performedi in conjunction wit one or more co-current depressurization, or equalization, steps wherein the equalization gas is not vented, but passed to another bed. When a co-current depressurization step is used, it can be performed either before, simultaneously with, or subsequent to the vent step. The effluent stream from the co-current depressurization step, which is comprised primarily of less readily adsorbable components, can be used to partially repressurize or purge another adsorber bed. The combination of the desorption effluent resulting from the counter-current depressurization step and the purge step are combined to have ethylene and heavier product purity of from about 20 to about 95 mol-%.

After the termination of the vent step and any desired co-current depressurization step(s), the adsorber bed is desorbed by reducing the pressure in a direction counter-current to the PSA feed direction to a desorption pressure that is preferably from about atmospheric pressure to about 3.5 kg/cm² absolute (about 50 psia). A portion of the desorption effluent stream recovered from the adsorption zone could be utilized as feed for the co-current displacement step following recompression.

A PSA cycle for a six-bed adsorption zone employing the vent, or co-current depressurization step following the adsorption step is shown in Table 1 below:

TABLE 1

| | | | | | | | | | | | |
|---|---|---|---|---|---|---|---|---|---|---|---|
| 1 | ADS | | VENT | | EQ1 | EQ2 | PP | BD | PUR | EQ2 | EQ1 | REP |
| 2 | EQ1 | REP | ADS | | VENT | | EQ1 | EQ2 | PP | BD | PUR | EQ2 |
| 3 | PUR | EQ2 | EQ1 | REP | ADS | | VENT | | EQ1 | EQ2 | PP | BD |
| 4 | PP | BD | PUR | EQ2 | EQ1 | REP | ADS | | VENT | | EQ1 | EQ2 |
| 5 | EQ1 | EQ2 | PP | BD | PUR | EQ2 | EQ1 | REP | ADS | | VENT | |
| 6 | VENT | | EQ1 | EQ2 | PP | BD | PUR | EQ2 | EQ1 | REP | ADS | |

Although any suitable PSA cycle known to those skilled in the art and incorporating the steps of adsorption, equalization, provide purge, purge and repressurization may be employed in the PSA operation, it is preferred to operate the PSA zone with a co-current desorption step, or vent step, immediately following the adsorption step to provide a second fuel gas stream which is employed to regenerate the dryer zone. Preferably, the vent step is terminated at a vent pressure which is at least about 700 kPa (about 100 psia).

When the separation zone comprises a membrane separation zone, the membrane employed is selective for the permeation of ethylene and heavier components and the non-permeate stream comprises hydrogen and methane. U.S. Pat. No. 5,879,431 B1, which is herein incorporated by reference, discloses the application of a rubbery and super glassy membrane at separation conditions which include a separation temperature between about 0° C. and about −100° C. for similar separations.

DETAILED DESCRIPTION OF THE DRAWINGS

The process of the present invention is hereinafter described with reference to FIGS. 1 and 2 which illustrate various aspects of the process. It is to be understood that no limitation to the scope of the claims which follow is intended by the following description. Those skilled in the art will recognize that these process flow diagrams have been simplified by the elimination of many necessary pieces of process equipment including some heat exchangers, process control systems, pumps, fractionation systems, etc. It may also be discerned that the process flow depicted in the FIGURES may be modified in many aspects without departing from the basic overall concept of the invention.

FIG. 1 illustrates the typical light olefins recovery scheme of the prior art. Referring to FIG. 1, an oxygenate conversion effluent stream in line 1 is passed to a compression zone 18 to raise the pressure of the oxygenate conversion effluent stream in line 1 to a demethanizer pressure of between about 1050 kPa (150 psia) and about 2860 kPa (400 psia) to produce a compressed effluent stream in line 5. More preferably, the compression zone raises the pressure of the oxygenate conversion effluent stream to produce a compressed effluent stream at a demethanizer pressure between about 1750 kPa (250 psia) and about 2450 kPa (350 psia). Generally, the compression zone 18 comprises a multi-stage compressor that, at a low interstage pressure, comprises a first interstage flash drum to remove a condensate stream in line 3 comprising primarily water and unconverted methanol that is returned to the oxygenate conversion reaction zone (not shown), and a second interstage flash drum to remove a $C_4$-plus stream in line 4 that is passed to a depropanizer (not shown) for further recovery of $C_3$ and $C_4$ hydrocarbons. The compressed effluent stream in line 5 is passed to an oxygenate removal zone 20 for the rejection of trace oxygenates including DME and methanol in line 6 that is returned to the oxygenate conversion reaction zone (not shown) and to produce an oxygenate removal zone effluent stream via line 7. The oxygenate removal zone effluent comprises less oxygenate than the oxygenate conversion effluent stream in line 5. Preferably, the oxygenate removal zone effluent comprises less than about 1000 ppm-wt oxygenates. The oxygenate removal zone effluent in line 7 is passed to a carbon dioxide removal zone 22 wherein carbon dioxide is absorbed by contacting a caustic solution or by contacting an amine solution in combination with a caustic solution (not shown) in a conventional manner to remove the carbon dioxide in line 8 dissolved in the spent absorbent to provide a carbon dioxide depleted stream in line 9 that is depleted in carbon dioxide relative to the oxygenate conversion zone effluent and is saturated with water. The carbon dioxide depleted stream in line 9 is passed to a dryer zone containing a solid desiccant to remove water (shown as line 10) from the carbon dioxide depleted stream in line 9 to produce a dry demethanizer feed stream in line 11. The demethanizer feed stream in line 11 is passed to a demethanizer zone 26 to provide a light hydrocarbon stream in line 13 comprising hydrogen, methane, carbon monoxide, ethylene and ethane, and a deethanized stream in line 12 comprising propylene, propane and $C_4$-plus olefins. The deethanized stream in line 12 is passed to further separation and recovery of propylene in a conventional manner (not shown) employing, for example, a depropanizer to separate the $C_3$ hydrocarbon from the heavier $C_4$-plus olefins and a $C_3$ splitter to provide a propylene product stream and a propane stream. The light hydrocarbon stream in line 13 is passed to a compression and selective saturation zone 28 to compress the light hydrocarbon stream to provide a compressed light hydrocarbon stream at a saturation pressure of about 2860 kPa (400 psia) and about 4200 kPa (600 psia). The compressed light hydrocarbon stream is contacted with a selective saturation catalyst in the presence of hydrogen to saturate any trace amount of acetylene which might be in the light hydrocarbon stream prior to passing the selectively saturated light hydrocarbon stream to a demethanizer zone 30 via line 14. Such selective saturation processes are well known to those skilled in the art. Because the selectively saturated light hydrocarbon stream in line 14 comprises hydrogen and methane, the demethanizer zone must be cooled with an ethylene chiller and be operated at a demethanizing temperature of between about −100° C. (−150° F.) and about −90° C. (−130° F.) in order to produce a $C_2$ hydrocarbon stream in line 16 comprising ethylene and ethane which can be further separated to produce a high purity ethylene product stream in a $C_2$ splitter column (not shown). An overhead stream comprising hydrogen and methane in line 15 is removed from the demethanizer zone 30 and withdrawn from the process as a fuel stream.

The present invention recognizes the unique character of the oxygenate conversion effluent stream, in particular that the light hydrocarbon stream comprises a non-adsorbable molar ratio of hydrogen and methane to $C_2$ hydrocarbons (ethylene and ethane) ranging from about 0.1 to about 0.5. According to the present invention, the demethanizer zone is operated at a significantly higher temperature (>−45° C.) to produce an overhead stream which now, in addition to hydrogen and methane, comprises some ethylene and ethane. This ethylene-depleted overhead stream is passed to a separation zone, or adsorption zone to recover the ethylene and return at least a portion of the recovered ethylene as a desorbed stream. The desorbed stream comprising the recovered ethylene is returned to be combined with the oxygenate conversion effluent stream. By this combined separation/fractionation scheme, the ethylene product stream is recovered at an overall recovery greater than about 99.5 mol-% relative to the ethylene in the oxygenate conversion zone effluent.

Figure 2:
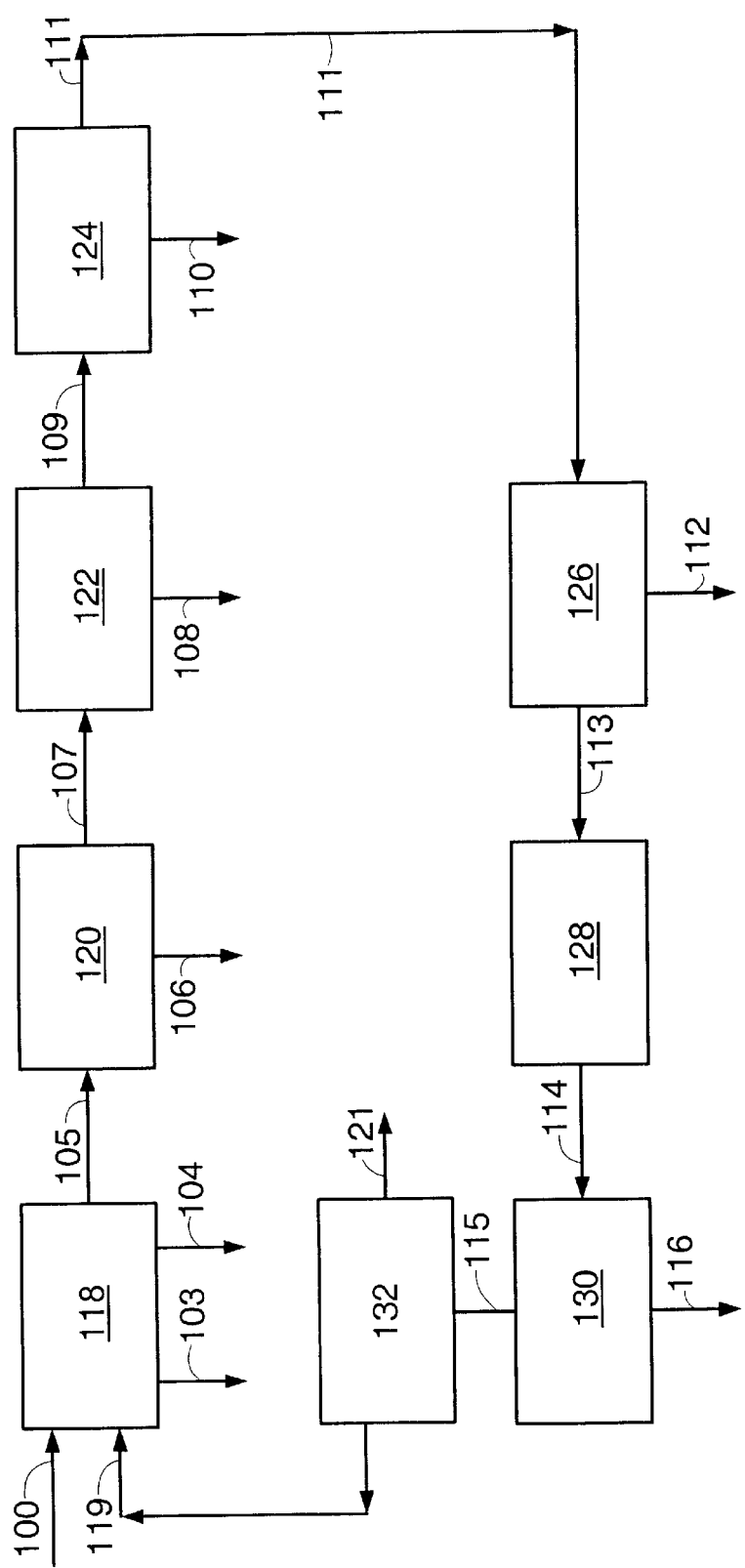
FIG. 2 is a schematic process flow diagram illustrating the process of the present invention.

Referring to FIG. 2, the oxygenate conversion effluent stream in line 100 is passed to a compression zone 118 to raise the oxygenate conversion effluent stream to the demethanizer pressure and produce a compressed effluent stream in line 105. As in FIG. 1, the compression zone 118 comprises a multi-stage compressor which recovers a condensate stream in line 103 comprising primarily water and methanol that is returned to the oxygenate conversion reaction zone (not shown) and a $C_4$-plus stream in line 104 that is passed to a depropanizer for further recovery of $C_4$ olefins. The compressed effluent stream in line 105 is passed to an oxygenate removal zone 120 to reject trace amounts of oxygenates which are depicted as being removed in line 106. Typically, the oxygenate removal zone 120 comprises a methanol wash to recover unreacted DME and trace oxygenates followed by a water wash zone to recover methanol and produce an oxygenate removal zone effluent stream in line 107 comprising less than about 1000 ppm-wt oxygenates. The oxygenate removal zone effluent stream in line 107 is passed to carbon dioxide removal zone 122 wherein carbon dioxide is absorbed by contacting a caustic solution or by contacting an amine solution in combination with a caustic solution in the conventional manner to remove carbon dioxide in line 108 dissolved in the spent absorbent to provide a carbon dioxide depleted stream in line 109. The carbon dioxide depleted stream in line 109 is passed to a dryer zone 124 to remove water of saturation depicted as a net water stream in line 110 to provide a dry demethanizer feed stream in line 111. The dryer comprises the cyclic operation of at least two beds containing a solid desiccant. The dryer beds are operated in a conventional sequence wherein one bed is removing water and the other bed is regenerated with a heated fuel gas stream (not shown). The demethanizer feed stream in line 111 is passed to a demethanizer zone 126 to provide a deethanized stream in line 112 comprising propylene, propane, and $C_4$-plus olefins, and a light hydrocarbon stream in line 113. The light hydrocarbon stream in line 113 which may comprise trace amounts of acetylene (i.e., comprising about less than 500 ppm-wt to less than about 100 ppm-wt acetylene) is passed to a compression and selective saturation zone 128 to compress the light hydrocarbon stream to a saturation pressure of between about 2860 kPa to about 4200 kPa and contact the compressed light hydrocarbon stream with a selective saturation catalyst in the presence of hydrogen to selectively saturate acetylene in a conventional manner to produce a selectively saturated light hydrocarbon stream in line 114. The selectively saturated light hydrocarbon stream, now comprising less than about 5 ppm-wt acetylene, and preferably comprising less than about 1 ppm-wt acetylene in line 114 is passed to a demethanizer zone 130 operated at a demethanizing temperature of about greater than −45° C. Preferably, the demethanizer zone 130 is operated at a demethanizer temperature greater than or equal to about −40° C. A C$_2$ hydrocarbon stream comprising ethylene and ethane is withdrawn in line 116 from the bottom of the demethanizer zone 130 which is passed to a C$_2$ splitter zone (not shown) for conventional separation as required to produce a high purity (>99.5 mol-%) ethylene product stream. An overhead stream in line 115 is withdrawn from the demethanizer zone 130 and passed to a separation zone 132, such as an adsorption zone 132 that during an adsorption step provides a fuel gas stream 121 comprising hydrogen and methane, and, during a desorption step, provides a desorption stream comprising ethylene in line 119. At least a portion of the desorption stream is recycled via line 119 to the compression zone 118 wherein the desorption stream is combined with the oxygenate conversion effluent stream in line 100, introducing the desorption stream at the appropriate stage of compression. The adsorption zone 132 comprises a PSA zone or a temperature swing adsorption zone or a combination thereof wherein the purge gas may be heated to improve the recovery of adsorbed olefins from the selective adsorbent. Preferably, the adsorption zone 132 comprises a PSA zone which includes a co-current depressurization step, or vent step, to produce a vent stream immediately following the adsorption step and wherein the adsorption effluent and at least a portion of the vent stream withdrawn during the vent step are combined to produce the fuel gas stream 121. Preferably, the vent gas pressure comprises a vent gas pressure greater than about 700 kPa (100 psia) so that a portion of the vent gas stream can be employed to regenerate the dryer zone (not shown).

The following examples are only used to illustrate the present invention and are not meant to be limiting.

EXAMPLES

Example I

In a conventional process arrangement as depicted in FIG. 1 (Prior Art), the demethanizer is operated with a condenser temperature of about −95° C. (−140° F.) and a pressure of about 3200 kPa (465 psia) in order to recover at least 99.6 mol-% of the ethylene in the demethanizer bottoms product. A cooling system for operating the demethanizer in the above manner is required to provide cooling for the demethanizer condenser and to provide for chilling the demethanizer feed to a temperature of about −68° C. (−90° F.). Pure ethylene refrigeration which can provide a cooling temperature of about −101° C. (−150° F.) and is generally used in this service. For an ethylene production rate of about 500,000 metric tonnes per year, the ethylene refrigeration system requires a centrifugal compressor with a capacity of about 4350 Nm$^3$/hr (2700 actual cubic feet per minute—inlet) at a capital cost of about 3.9 million dollars. For an ethylene production rate of about 120,000 metric tonnes per year, the ethylene refrigeration system requires two reciprocating compressors, each with a capacity of about 1030 Nm$^3$/hr (640 actual cubic feet per minute-inlet) at a capital cost of about 1.9 million dollars. Thus, the ethylene refrigeration system represents a significant capital cost, a large portion of which is directly related to simply compressing the ethylene.

Example II

An engineering simulation of the demethanizer operating as shown in FIG. 2 according to the present invention indicates that the demethanizer can be operated at an overhead temperature of about −40° C. (−40° F.) to provide about an 85 mol-% ethylene recovery and that this operation can be combined with a PSA zone containing silica gel as the selective adsorbent for the recovery of ethylene and ethane. The PSA zone recovers about 97.8 mol-% ethylene and about 20.5 mol-% methane. The ethylene-rich PSA tail gas is returned to the first stage of the oxygenate conversion compressor zone at a desorption pressure of about 117 kPa (17 psia). The overall recovery of the ethylene from the complex is greater than about 99.6 percent. The demethanizer bottoms comprises ethylene and ethane which is passed to an appropriate C$_2$ splitter for the production of high purity or polymer grade ethylene.

Example III

A comparison is shown in Table 1 of the relative equipment size or capacity for the prior art scheme of FIG. 1 and the scheme of the present invention as depicted in FIG. 2. The relative size is expressed in term as a percent larger or smaller than the base case. Although the PSA inclusive scheme of the present invention required small increases in the compression capacity and process compressors, the ethylene compressor is completely eliminated. The capacity of the compressors is expressed in energy requirements and the size differences are expressed in terms of relative column inside diameter. The PSA case represents an overall capital cost savings of about 3.2 million dollars for a 120,000 metric tonnes per year ethylene production and about a 73,000 dollars per year utility savings.

| Process Equipment: | Factor: | Base Case: | PSA Case: |
|---|---|---|---|
| Reactor Effluent Compressor | Capacity | 100. | 110 |
| Acetylene Feed Compressor | Capacity | 100. | 117 |
| Propylene Refrigeration | Capacity | 100. | 96 |
| Ethylene Refrigeration | Capacity | 100 | 0 |
| DME Adsorber | Diameter | 100. | 106 |
| DME Stripper | Diameter | 100. | 85 |
| Methanol Adsorber | Diameter | 100. | 105 |
| Caustic Scrubber | Diameter | 100. | 105 |
| Demethanizer | Diameter | 100. | 95 |
| Deethanizer | Diameter | 100. | 107 |
| Depropanizer | Diameter | 100. | 92 |
| Debutanizer | Diameter | 100. | 103 |
| Dryer Capacity | Diameter | 100. | 101 |

Example IV

Figure 3:
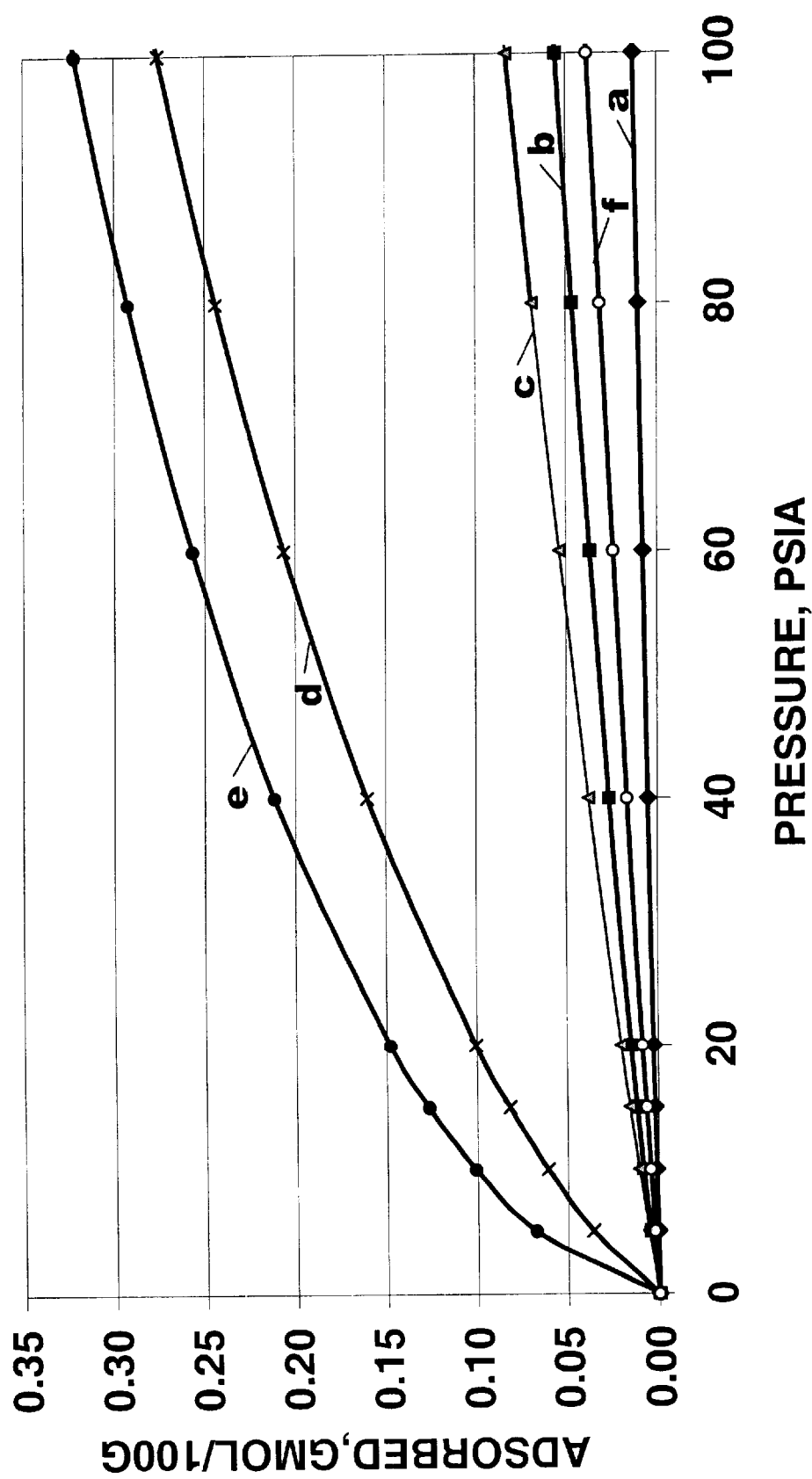
FIG. 3 is a chart of adsorption isotherms for components of demethanizer overhead on silica gel.

Adsorption isotherms for the individual components typically found in the overhead stream withdrawn from a demethanizer operating according to the present invention are shown in FIG. 3 for adsorption on silica gel at an adsorption temperature of about 15° C. (60° F.). Isotherm data is shown for the following components: hydrogen(a), carbon monoxide(b), methane(c), ethane(d), ethylene(e) and nitrogen(f). In FIG. 3, the ethylene and ethane isotherms indicate a high selectivity over hydrogen, methane and carbon monoxide over the silica gel adsorbent. This adsorption isotherm data were developed using standard high-pressure Sartorius microbalance techniques well known to those skilled in the art.

Example V

Figure 4:
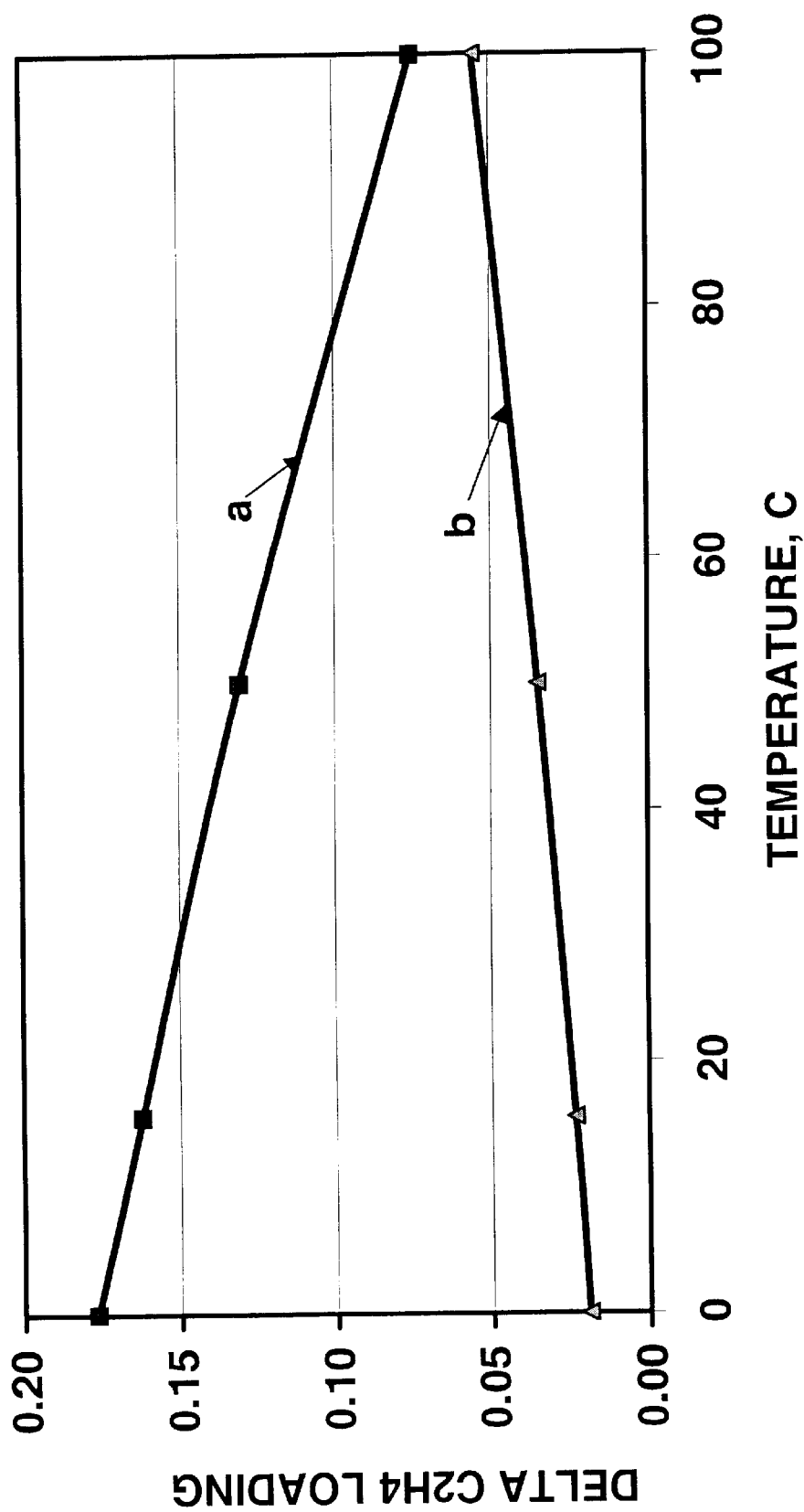
FIG. 4 is a chart of adsorbent delta loadings comparing silica gel and zeolite 4A over a range of adsorption temperatures.

Based on adsorption isotherm data developed from standard high-pressure Sartorius microbalance techniques for ethylene adsorption over silica gel and a zeolite 4A adsorbent, delta loadings expressed in grams/100 grams of adsorbent for the silica gel (a) and the 4A zeolite (b) at temperatures ranging from about 0° C. to about 100° C. were calculated and are presented in FIG. 4. Of note is the greater delta loading or adsorption capacity for silica gel relative to the delta loading of the zeolite 4A at adsorption temperatures less than about 100° C. Surprisingly, the delta loading of ethylene on the silica gel increases at adsorption temperatures less than about 100° C., while the delta loading values for the zeolite 4A are initially lower than that of the silica gel at 100° C. and gradually decrease for temperatures below 100° C.

Example VI

Figure 5:
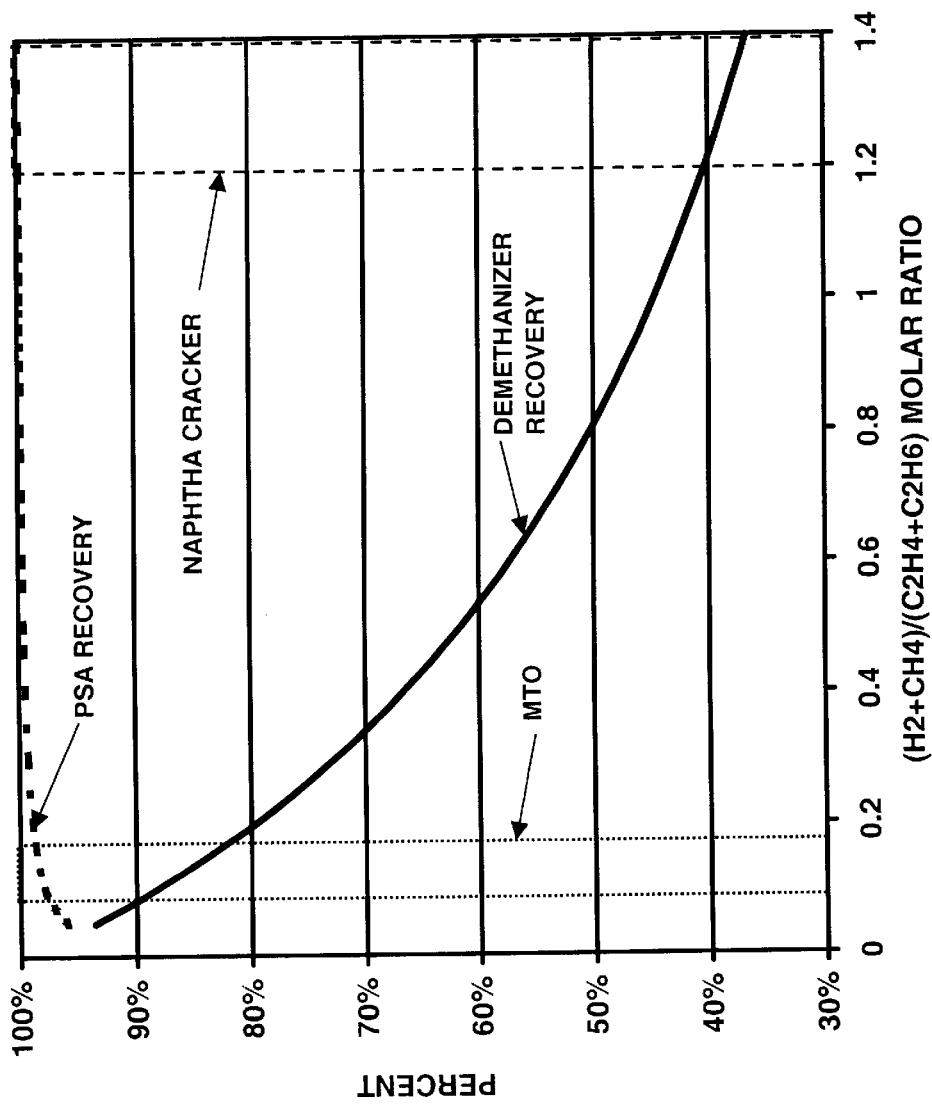
FIG. 5 is a chart of the relative ethylene recovery required in a PSA and in the demethanizer for a range of demethanizer overhead composition.
Figure 6:
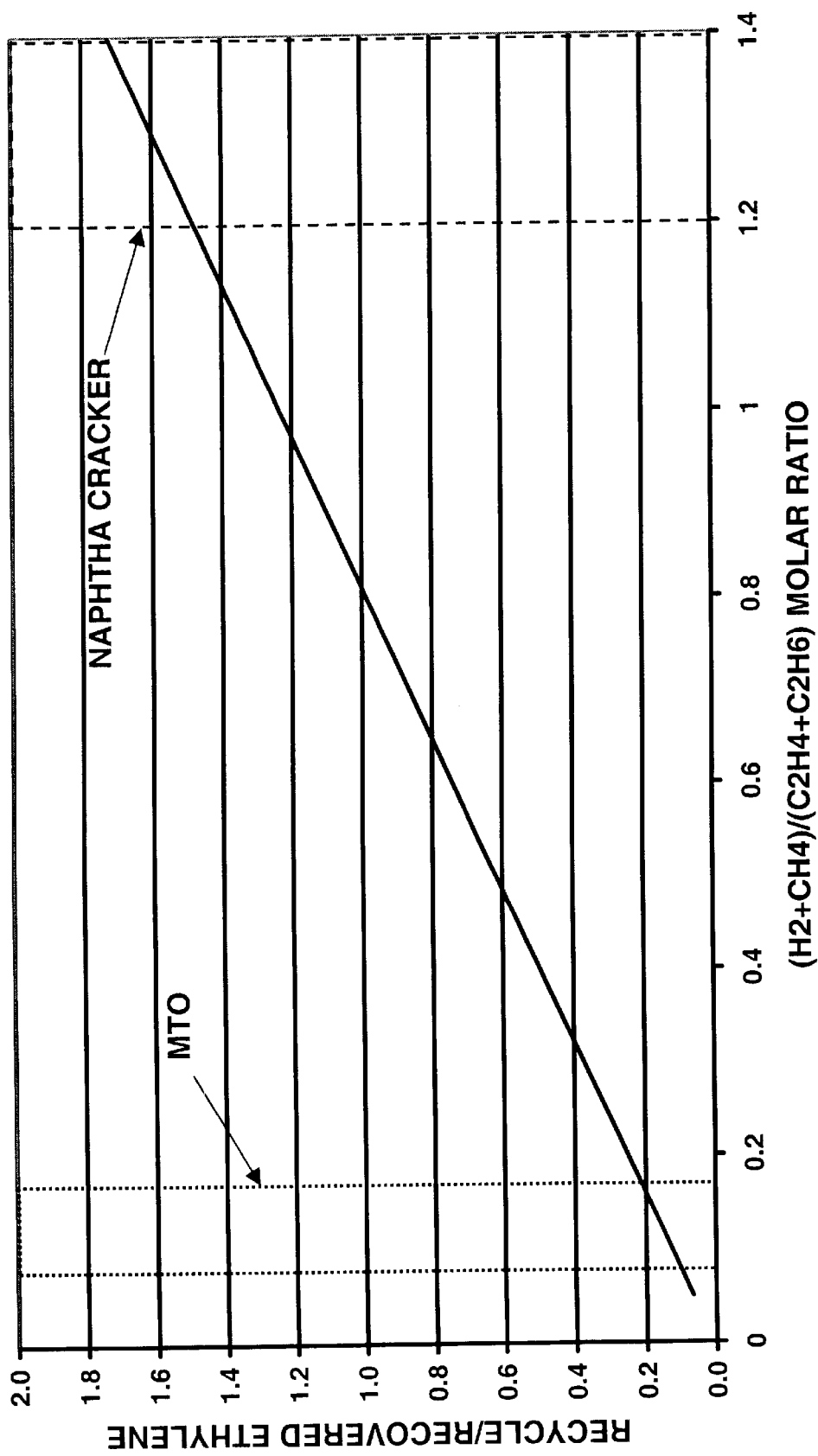
FIG. 6 is a chart of the ratio of ethylene recycled to the ethylene recovered over a range of demethanizer overhead composition.

The operation of the demethanizer of the present invention operating at a demethanizer temperature of about −40° C. as shown in FIG. 2 can be carried out over a range of recoveries according to the ratio of hydrogen and methane to $C_2$ hydrocarbons in the overhead stream. FIG. 5 illustrates the recovery of ethylene decreases as the non-adsorbable molar ratio of hydrogen and methane to $C_2$ hydrocarbons increases. When the ratio falls within a range of about 0.07 to about 0.17 as produced in the MTO schemes, the recovery of the demethanizer is greater than about 85 percent and the PSA recovery is less than about 99 percent. If the overhead stream comprises a composition corresponding to a conventional naphtha cracker or pyrolysis ethylene plant, the non-adsorbable molar ratio comprises a value above 1.2 which reduces the demethanizer recovery to less than about 40 percent and requires the PSA to recover essentially all of the ethylene. FIG. 6 illustrates the consequence of these operations on the overall complex. For a non-adsorbable molar ratio as produced in the effluent of oxygenate conversion zones which ranges less than about 0.5, the amount of ethylene recycled in the overall complex is less than about 60 percent of the total ethylene product. As the non-adsorbable molar ratio increases to about 1.2, the amount of ethylene recycled in the complex approaches 150 percent of the ethylene product produced, resulting in significantly greater capital and operating cost requirements.

What is claimed is:

1. A process for the production of an ethylene product stream front an oxygenate conversion effluent stream comprising hydrogen, methane, ethylene, ethane, propylene, propane, and $C_4$-plus olefins said process comprising:

a) passing the oxygenate conversion effluent stream to a deethianizer zone to provide a light hydrocarbon feedstream comprising hydrogen, methane, ethylene and ethane, and a deethanized stream comprising propylene, propane, and $C_4$-plus olefins;

b) passing the light hydrocarbon stream to a demethanizer zone operating at a demethanizing temperature greater than about −45° C. to provide a bottom stream comprising ethylene and ethane and an overhead stream comprising hydrogen, methane, and ethylene;

c) passing the overhead stream at effective adsorption conditions to an adsorption zone containing at least two adsorption beds, each of said adsorption beds containing a selective adsorbent to adsorb the ethylene on adsorption to produce an adsorber effluent stream comprising hydrogen and methane, and on desorption to produce a desorbed stream comprising ethylene and immediately following adsorption withdrawing a vent stream comprsing hydrogen and methane in a cocurrent depressurization step which is terminated prior to the breakthrough of ethylene;

d) passing the bottom stream to a $C_2$ splitter zone to produce the ethylene product stream and an ethane stream; and e) combining the desorbed stream with the oxygenate conversion effluent stream prior to passing the oxygenate conversion effluent stream to the demethanizer zone.

2. The process of claim 1 wherein the effective adsorption conditions include an adsorption temperature comprising less than about 49° C. (120° F.).

3. The process of claim 1 wherein the selective adsorbent is selected from the group consisting of silica gel, activated carbon, alumina, zinc X zeolite, calcium Y zeolite and mixtures thereof.

4. The process of claim 1 wherein the adsorption zone comprises a pressure swing adsorption zone.

5. The process of claim 1 wherein the demethanizing temperature comprises a temperature greater than about −40° C.

6. The process of claim 1 wherein the selective adsorbent comprises silica gel.

7. The process of claim 1 wherein the light hydrocarbon stream comprises a non-adsorbable molar ratio of hydrogen and methane to $C_2$ hydrocarbons of less than about 0.5 moles of hydrogen and methane to moles of ethylene and ethane.

8. The process of claim 1 wherein the light hydrocarbon stream comprises a non-adsorbable molar ratio of hydrogen and methane to $C_2$ hydrocarbons ranging from about 0.01 to about 0.5 moles of hydrogen and methane to moles of ethylene and ethane.

9. The process of claim 1 wherein the ethylene product stream is recovered at a recovery of greater than about 99.5 mol-% relative to the ethylene in the oxygenate conversion effluent stream.

10. The process of claim 1 further comprising compressing the oxygenate conversion effluent stream to an effective demethanizer pressure of between about 1050 kPa and about 2860 kPa prior to passing the oxygenate conversion effluent stream to the demethanizer zone.

11. The process of claim 1 wherein the ethylene product stream comprises about 99.5 mol-% ethylene or greater.

12. The process of claim 1 wherein the demethanizer zone comprises a primary ethylene recovery of greater than about 85 mol-% ethylene per mole of ethylene in the light hydrocarbon stream.

13. The process of claim 1 wherein the adsorption zone provides an adsorptive recovey of ethylene comprising greater than about 95 mol-% ethylene.

14. The process of claim 1 further comprising recovering a propylene product stream from the deethanized stream.

15. The process of claim 1 wherein the demethanizer zone is refrigerated to the demethanizing temperature with a refrigerant comprising propylene.

16. The process of claim 1 wherein the oxygenate conversion effluent stream comprises a reaction product of an oxygenate feedstock having been reacted at effective conversion conditions in the presence of a diluent in an oxygenate conversion reaction zone containing a small pore, non-zeolitic catalyst to convert essentially all of the oxygenate feedstock to produce the oxygenate conversion effluent stream.

17. The process of claim 1 wherein the oxygenate conversion effluent stream further comprises carbon dioxide and said process further comprises passing the oxygenate conversion effluent stream to a carbon dioxide removal zone to remove at least a portion of the carbon dioxide and subsequently passing a carbon dioxide depleted stream to a dryer zone containing a solid desiccant to remove water prior to passing the oxygenate conversion effluent stream to the demethanizer zone.

* * * * *

UNITED STATES PATENT AND TRADEMARK OFFICE
CERTIFICATE OF CORRECTION

PATENT NO. : 6,444,869 B2
DATED : September 3, 2002
INVENTOR(S) : John J. Senetar et al.

It is certified that error appears in the above-identified patent and that said Letters Patent is hereby corrected as shown below:

Column 17,
Line 40, replace "front" with -- form --.
Line 44, replace "deethianizer" with -- deethanizer --.
Line 62, replace "comprsing" with -- comprising --.

Signed and Sealed this

Fifteenth Day of October, 2002

Attest:

JAMES E. ROGAN
Attesting Officer   Director of the United States Patent and Trademark Office